United States Patent [19]

Audeh

[11] Patent Number: 4,771,030

[45] Date of Patent: Sep. 13, 1988

[54] PROCESS FOR PREPARING PARTICULATE ALUMINUM METAL FOR ADSORBING MERCURY FROM NATURAL GAS

[75] Inventor: Costandi A. Audeh, Princeton, N.J.

[73] Assignee: Mobil Oil Corporation, New York, N.Y.

[21] Appl. No.: 118,701

[22] Filed: Nov. 9, 1987

Related U.S. Application Data

[62] Division of Ser. No. 944,136, Dec. 22, 1986, Pat. No. 4,717,399.

[51] Int. Cl.$^4$ .................... B01J 20/30; B01J 21/02; B01J 27/125; B01J 27/25
[52] U.S. Cl. .................................. 502/414; 423/210; 502/201; 502/226; 502/341; 502/345

[58] Field of Search ............... 502/414, 201, 301, 341, 502/226, 355; 423/210

[56] References Cited

U.S. PATENT DOCUMENTS 2,981,696  4/1961  Hervert et al. ...................... 502/226
4,717,399  1/1988  Audeh .................................... 55/72

Primary Examiner—Paul E. Konopka
Attorney, Agent, or Firm—Alexander J. McKillop; Michael G. Gilman; Van D. Harrison, Jr.

[57] ABSTRACT

Hydrocarbon gases containing trace quantities of mercury are treated to remove the mercury by contacting the gases with a porous bed of aluminum which has been activated by contacting it with an aqueous solution of a soluble mercuric salt and subsequent drying of the activated bed in a non-oxidizing atmosphere.

2 Claims, No Drawings

PROCESS FOR PREPARING PARTICULATE ALUMINUM METAL FOR ADSORBING MERCURY FROM NATURAL GAS

This is a division of copending application Ser. No. 944,136 filed on Dec. 22, 1986, now U.S. Pat. No. 4,717,399, issued Jan. 5, 1988.

NATURE OF THE INVENTION

This invention relates to a method for purifying and removing trace amounts of mercury from natural gas. In another aspect this invention relates to a method for treating an absorbent to enable it to adsorb mercury from a gas stream.

PRIOR ART

Trace quantities of mercury are known to exist in natural gases but the significance of these trace quantities has not been recognized until recently. The mercury detected in the produced gas is now known not to result from well drilling or well completion operations and does not result by accident in the gas stream. The mercury is produced in association with the gas and is thought to originate from geologic deposits in which the natural gas occurs. Even in trace quantities however, mercury is an undesirable component of natural gas. The processing of natural gas in LNG plants requires at some location in the system contact with equipment made primarily of aluminum. This is particularly true after the stages of processing where the gas is treated to remove carbon dioxide and hydrogen sulfide and then is chilled or cooled in aluminum-constructed heat exchangers. Because large volumes of gas must flow through the aluminum heat exchangers they are of massive size and represent a capital investment of several million dollars. Damage to these exchangers is to be avoided if at all possible. One threat of damage comes from the mercury present in the gas flowing through the heat exchangers. Although the concentration of mercury appears low, its effect is cumulative as it amalgamates with the aluminum. The result is damage to the system such as corrosion cracking leading to equipment failure, fires and similar catastrophe. Repair is correspondingly difficult because of damage to the welded seams of the aluminum. Replacement of the heat exchangers in an LNG plant represents a large expenditure. The problem of mercury in natural gas is discussed further in U.S. Pat. No. 4,094,777 and French Pat. No. 2,310,795, both of which are incorporated herein by reference.

Several methods have been proposed for absorbing mercury from natural gas. For example, J. E. Leeper in Hydrocarbon Processing, Volume 59, November, 1980, pages 237-240, describes a procedure wherein natural gas is contacted with a fixed bed of copper sulfide on an alumina-silica support to remove the mercury present. The absorbent is regenerated by purging it with gas heated to a temperature of 200°-500° C. Another commercial process is based on contacting the mercury contaminated gas with sulfur supported on activated carbon. According to the Leeper article, the sulfur impregnated activated charcoal process is regarded as the best system for treating a gas stream, particularly one free of heavy hydrocarbons. The reference, Hydrocarbon Processing, Volume 59, November, 1980, pages 237-240, is incorporated herein by reference.

A primary object of this invention is to provide an improved process for removing trace quantities of mercury present in a gas, particularly a natural gas. Still another object of this invention is to provide a process wherein the resulting adsorbent need not be regenerated but can be utilized as is for other processes.

SUMMARY OF THE INVENTION

Briefly stated, this invention comprises contacting aluminum metal shavings or other forms of particulated aluminum metal or aluminum sponge with an aqueous solution of mercuric chloride thereby sensitizing or activating the aluminum metal surfaces for subsequent contact with mercury. Natural gas containing mercury is flowed through a bed of the treated aluminum to remove the mercury from the natural gas.

DESCRIPTION OF THE INVENTION

The aluminum shavings utilized in this invention can be of any desired size or shape. Preferably they will range in size from 1/16" to ¼". The aluminum shavings are packed in a container vessel constructed of material that will not react with the mercury present in the natural gas to be processed and which has the strength to withstand process conditions. The vessels should be designed so that air can be excluded. The pack of aluminum shavings (or aluminum sponge) is first flushed with an aqueous solution of mercuric chloride ($HgCl_2$) or mercuric nitrate or any water soluble mercuric salt. The aqueous solution preferably contains between 0.001 to 5.0 grams or a saturated solution of dissolved mercuric chloride or water soluble mercuric salt per liter of water. The solution should be circulated through the pack for about 30 minutes. After this step, the bed is dried by flowing through it a stream of natural gas. It is important to avoid introducing air or other oxygen containing gas into the bed since the oxygen will form an aluminum oxide coating making the mass of aluminum particles ineffective and will thus defeat the purpose of the treatment. For this reason a non-oxidizing atmosphere is essential. The temperature of drying should be between 45° and 95° C.

The bed of metal aluminum shavings is then ready for the process of removing trace quantities of mercury from natural gas. This is effected by circulating the natural gas through the body of activated aluminum shavings until a sufficient amount of mercury has been alloyed or deposited on the aluminum shavings. The time required for this will depend on the concentration of the mercury in the gas stream, the amount of aluminum shavings, and the overall design of the treating system.

When the activated aluminum metal has no longer any capability to adsorb mercury from the gas stream it is removed from use in the system and a new activated bed of aluminum shavings is put into service. The spent bed of aluminum shavings still has utility however for additional chemical processes. These processes are those for preparing organic aluminum compounds utilizing mercury amalgam. For example, aluminum alkoxides can be prepared by the reaction of aliphatic alcohols with aluminum amalgam. In the preparation of these alkoxides the mercury is not consumed and can be reclaimed by vacuum distillation. This particular process described above provides the advantage that the adsorbent need not be regenerated. It can be simply replaced by another bed of adsorbent and used in a subsequent reaction for an entirely different purpose if such is desirable.

What is claimed is:

1. A method for preparing a body of particulate aluminum metal for absorbing mercury comprising contacting said body of material with an aqueous solution containing between about 0.001 and about 5 grams per liter of a soluble mercuric salt for a period of between about 0.1 and about 1 hour at a temperature between about 65° and about 180° F. and drying the resulting activated mass in a non-oxidizing atmosphere at a temperature between about 45° and about 95° C.

2. The method of claim 1 wherein the mercuric salt is selected from the group consisting of mercuric chloride and mercuric nitrate.

* * * * *